United States Patent [19]
Heiser

[11] Patent Number: 5,971,753
[45] Date of Patent: Oct. 26, 1999

[54] ORTHODONTIC BRACKET

[76] Inventor: Wolfgang Heiser, Dr.-Stumpf-Strasse 73 A-6020, Innsbruck, Austria

[21] Appl. No.: 09/229,920

[22] Filed: Jan. 13, 1999

Related U.S. Application Data

[63] Continuation-in-part of application No. 09/031,248, Feb. 26, 1998, Pat. No. 5,890,893.

[51] Int. Cl.$^6$ .................................................. A61C 3/00
[52] U.S. Cl. ................................ 433/11; 433/13; 433/14
[58] Field of Search ................................... 433/8, 10, 11, 433/13, 14

[56] References Cited

U.S. PATENT DOCUMENTS

| | | |
|---|---|---|
| 3,871,096 | 3/1975 | Wallshein . |
| 4,144,642 | 3/1979 | Wallshein . |
| 4,192,070 | 3/1980 | Lemchen . |
| 4,283,908 | 8/1981 | Kurz . |
| 4,415,330 | 11/1983 | Daisley et al. . |
| 5,022,854 | 6/1991 | Broughton . |
| 5,074,783 | 12/1991 | Reher . |
| 5,356,288 | 10/1994 | Cohen . |
| 5,474,446 | 12/1995 | Wildman et al. . |
| 5,562,444 | 10/1996 | Heiser et al. . |
| 5,711,666 | 1/1998 | Hanson . |
| 5,890,893 | 4/1999 | Heiser . |

*Primary Examiner*—Nicholas D. Lucchesi
*Attorney, Agent, or Firm*—Morgan & Finnegan, L.L.P.

[57] ABSTRACT

An orthodontic bracket having an archwire slot includes a arc-shaped leaf spring capable of exerting a lateral force onto an archwire inserted into the archwire slot. The leaf spring is secured to a structure of said bracket at positions spaced along the slot. The bracket may have a slider plate to close the slot to avoid ligatures. In another embodiment the structure comprises an undercut holding the archwire in a position defined by the pressure exerted by the leaf spring. A bent slider may be interposed between said leaf spring and the archwire.

12 Claims, 12 Drawing Sheets

ORTHODONTIC BRACKET

This application is a continuation-in-part of my U.S. patent application Ser. No. 09/031,248, filed Feb. 26, 1998 now U.S. Pat. No. 5,890,893.

BACKGROUND OF THE INVENTION

1. Field of the Invention

The invention refers to a bracket for producing tooth movement in the treatment of dental malocclusions.

2. Description of the Related Art

Orthodontic brackets comprising a base plate for attachment to the crown of a tooth and comprising a structure attached to the base plate, elevated over the base plate, said structure having at least one slot for receiving an archwire are generally known and described e.g. in U.S. Pat. No. 5,562,444 (Heiser et al.), U.S. Pat. No. 5,074,783 (Reher), U.S. Pat. No. 5,022,854 (Broughton) and U.S. Pat. No. 4,415,330 (Daisley et al.), the contents thereof are incorporated in this specification by reference.

For the orthodontic treatment of a patient having malposed teeth, the brackets of a complete set of brackets are attached in predetermined positions at the crowns of the teeth of the patient, e.g. by the aid of a cement or adhesive, and subsequently, a common archedly extending archwire is inserted into the archwire slots in the structures of the brackets of a jaw so that the brackets are lined up on the archwire like pearls on a string, see e.g. FIG. 1 in U.S. Pat. No. 4,283,908 (Kurz). The archwire is secured in the slots of the brackets by means of ligatures or my means of closing springs, see e.g. the U.S. Pat. No. 5,562,444 (Heiser et al.).

The brackets are mounted on the crowns of the teeth in a manner that they each have a predetermined orientation with respect to the tooth, see e.g. the U.S. Pat. No. 5,022,854 (Broughton), according to which imaginary prolongation lines of the lateral edges, i.e. sight lines, of the specially formed base plate of the bracket intersect in the tip of the root of the respective tooth. According to the malposition of the teeth of the patient to be overcome, the archwire inserted into the bracket slots at the beginning of the orthodontic treatment has an irregular, more or less waved or angled extension.

Caused by the resiliency of the archwire, the archwire exerts a torque onto the brackets and consequently onto the teeth, which, due to the durability of its influence finally causes the teeth to yield and gradually move to a proper position determined by the orthodontist so that at the end of the orthodontic treatment the archwire connecting the brackets substantially extends in a straight line apart from its arched extension following the arched shape of the jaw.

If the malpositions of the teeth are too great, a relatively thin archwire is sufficient at the beginning of the treatment to cause the required torque at the teeth. An archwire that is too thick would cause an excessive torque. The more the tooth position approaches the proper position, the thicker the archwire must be to exert the torque necessary for moving the teeth. Thus, the archwires are exchanged several times during an orthodontic treatment. However, the brackets are not exchanged. The latter are dimensioned such that the thickest possible archwire can still be received in archwire slots of the brackets.

The movement tolerance or malposition tolerance, that can be comprised by means of an orthodontic treatment of this kind is approximately 15° angle of rotation at the tooth. However, a thin archwire, as it is used at the beginning of the treatment, has a clearance of movement within the slot of each bracket of approximately 8°, so that under certain circumstances an effective angle of rotation of 7° only remains about which the tooth can be rotated by means of said thin archwire. This was taken into account and compensated for by an early exchange of the thin archwire against a thicker one.

The frequent exchange of the archwires is a nuisance for the patient and requires a lot of time, and it is also very expensive because of the medical treatment.

SUMMARY OF THE INVENTION

The object of the invention is to provide a bracket of the above-mentioned kind in which the success of the treatment can be improved and the number of archwire exchanges can be reduced.

The invention provides a bracket which has a pressure spring capable of pressing an archwire inserted into the slot transversely to the axis thereof and substantially parallel to the base plate of the bracket in a defined abutment to one of the lateral walls of the archwire slot. Hereby the clearance in the transverse direction, which an archwire of smaller cross sectional dimensions than the bracket slot has within the slot, is compensated or received.

A comparatively thin archwire is therefore capable over a longer period of time compared to the prior art to cause a torque at the brackets which is transferred to the teeth and which leads to an intended movement of the teeth in the direction toward a proper position. The number of archwire exchanges can therefore be reduced compared to the prior art.

The invention can be used for all brackets, no matter how the archwire is secured in the slot against sliding out. Means of that kind can e.g. be ligatures that are wound around the tie wings of the bracket structure and that extend over the archwire, or closing springs, that press onto the archwire from top. "Top" means in this case the side of the bracket opposite the base plate.

In a particular embodiment of the invention, it is even possible to completely refrain from using separate closing springs or ligatures of the above-mentioned kind for securing the archwire within the slot of the bracket. According to said embodiment, the lateral wall of the archwire slot against which the archwire is pressed by the pressure spring, is undercut. The undercut is delimited toward the top by a projection under which the archwire is pressed by the pressure spring and which in cooperation with the spring therefore prevents the archwire from sliding out of the slot.

According to an especially preferred embodiment, the pressure spring, that shall laterally press against the archwire, is a leaf spring, which has two ends and which is clamped into the bracket structure at two positions spaced in the longitudinal direction of the archwire, so that it is curved and projects from the side through an opening in the bracket structure into the archwire slot so far that it can laterally urge against an archwire located in the slot.

The bracket structure in this case is, according to an advantageous embodiment, designed such that the pressure spring can be forced from the described active position by means of a simple, mandrel-shaped tool into a release position that is mirror-inverted thereto, in which it is completely out of the slot.

In an especially preferred embodiment of the invention, a slide plate is used for securing the archwire in the bracket slot, said slide plate being slidably retained at the bracket structure and being capable of being slid over and away from the slot, and said curved leaf spring is mechanically coupled with the slide plate. When displacing the slide plate into the closing position covering the slot, the leaf spring is moved from its release position which is a first stable position over its instable balance point to its active position which is a second stable position, urging against the archwire, in which at the same time it secures the slide plate in its closing position. On the other hand, in the opposite, mirror-inverted bent first position of the leaf spring, it secures the slide plate in its open position, so that the orthodontist may easily insert the archwire into the open archwire slot or may remove it therefrom without any risk that the slide plate moves unintentionally.

The invention can be realized in a very simple manner. When using a leaf spring as a pressure spring, two bearings only have to be formed at the bracket structure between which the leaf spring is clamped.

The invention also enables the orthodontist to influence the torque caused by the archwire at individual teeth individually, i.e. individually for each tooth, in that according to the respective need, it brings the pressure spring into pressure engagement with the archwire (first stable position) or not (second stable position).

DETAILED DESCRIPTION OF THE DRAWINGS

The invention will now be described with reference to embodiments shown in the drawings.

DETAILED DESCRIPTION OF THE INVENTION

Before explaining the invention, it is to be noted that the embodiments of FIGS. 1 to 16 as far as the utilization of an arched spring the ends of which are movably secured in pocket bores are subject matter of the claims in my U.S. patent application Ser. No. 09/031,248 above.

Figure 1:
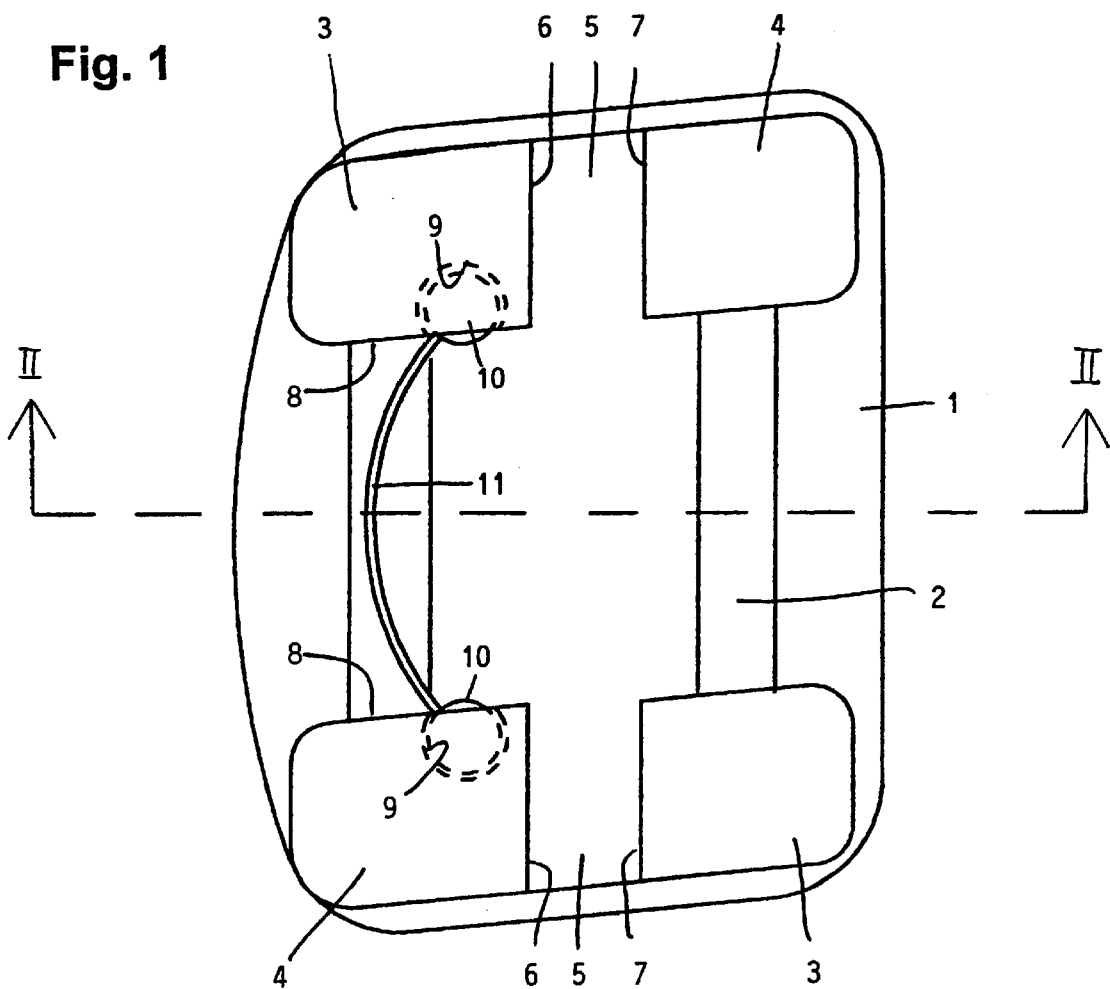
FIG. 1 is a top view onto a bracket according to a first embodiment of the invention in open condition of the pressure spring.
Figure 2:
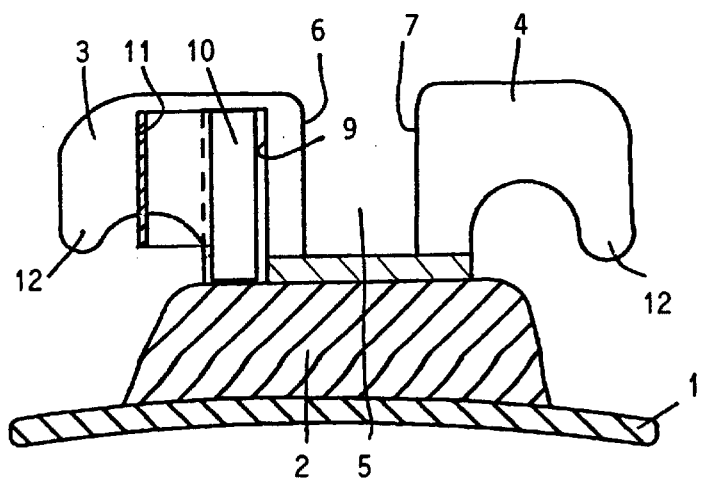
FIG. 2 is a sectional view of the bracket of FIG. 1, cut along the line II—II of FIG. 1.

FIG. 1 and 2 show a first embodiment of a bracket from the top. On a base plate 1, which is determined for fixing the bracket at the crown of a tooth, a structure is attached, consisting of a base 2, with two pairs of wings 3 and 4 projecting therefrom. The pairs of wings 3, 4 are arranged at a mutual spacing, so that they form a slot 5 between both, which in this case consists of two sections spaced by an opening. The slot 5 serves for receiving an archwire (not shown). Each slot section is limited on both sides by side walls 6 and 7, which form the lateral limitation of the pairs of wings 3 and 4 on sides facing one another.

One bearing 9 each is provided at the two wings 3 of the first pair of wings at the sides facing each other. The ends 10 of a leaf spring 11 are held in these bearings 9, said leaf spring 11 having a total length that is greater than the free distance between the bearings 9. In this manner, the leaf spring 11 mounted in the bearings 9 adopts the arc-like shape shown in FIG. 1 and has two stable conditions, one of which being the open condition shown in FIG. 1. In the other, closed condition, which is shown in FIG. 3, the leaf spring 11 extends in mirror-inverted fashion to the condition of FIG. 1, reflected at an imaginary connection plane extending through the bearings.

The bearings 9 are pocket bores in the embodiment according to FIG. 1 to 4, which are open at the lateral surfaces 8 of the wings facing one another for penetration of the leaf spring 11 and which were formed, e.g. drilled parallel to one another into the wings from the bottom, i.e. from the side facing the base 2.

Figure 3:
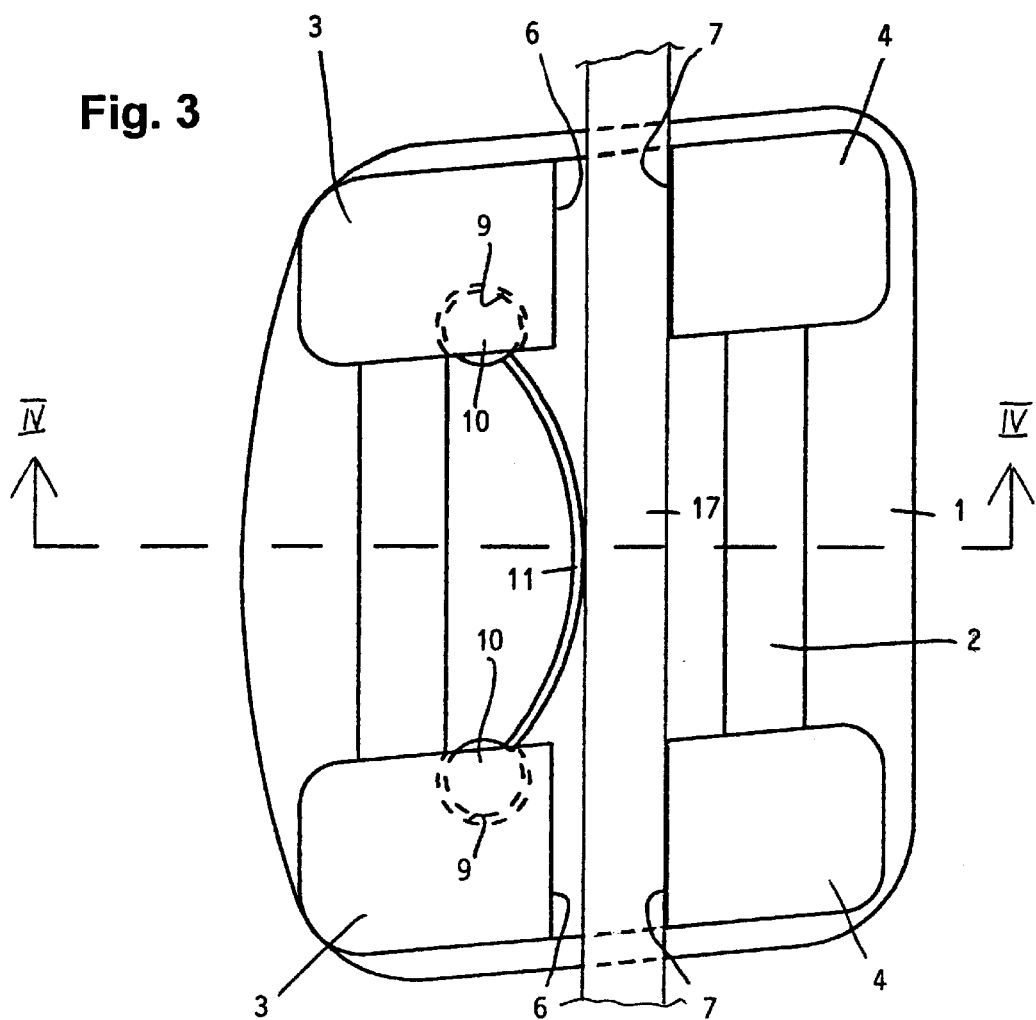
FIG. 3 is a top view onto the bracket of FIG. 1 in closed condition of the pressure spring and with an archwire inserted.
Figure 4:
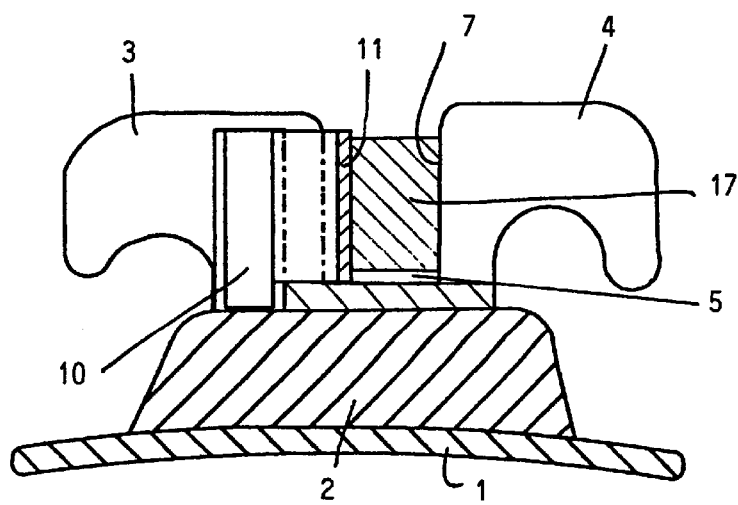
FIG. 4 is a sectional view of the bracket of FIG. 3, cut along the line IV—IV of FIG. 3.

The ends 10 of the leaf spring 11 may be rolled or may be formed to a cylindrical shape by fusing, as is shown in FIG. 1 and 3. The leaf spring 11 in this embodiment is inserted into the bearings 9 from the bottom, before the base 2 is connected to the pairs of wings. The leaf spring 11 is in this manner irremovably held on the bracket.

Use of this bracket is now explained.

FIG. 1 and 2 show the bracket in open stable condition of the leaf spring 11. In this first position of the leaf spring, an archwire 17 may be inserted into the slot 5, said archwire being not shown in FIG. 1 and 2, but may be seen in FIG.

3 and 4. After inserting the archwire 17 into the slot 5, the leaf spring 11 is brought into a second stable position by the orthodontist by means of a small tool, e.g. a needle, said second position being shown in FIG. 3 and corresponding to the closing position in which the leaf spring 11 presses against the archwire 17, which is why it was previously called "pressure spring", so that the archwire 17 is urged into a defined abutment to the walls 7 of the second pair of wings 4.

Finally, the archwire is secured in the slot 5 for example by winding a ligature (not shown) about the wings 3 and 4 and over the archwire 17. For fixing the ligature to the wings 3 and 4, these wings are provided with downwardly projecting horns, see FIG. 2, which hold the ligature. This feature and the attachment of the ligature are generally known to the person skilled in the art, so that a drawing is not required.

FIG. 5 to 8 show a second embodiment of the invention, which differs from the first embodiment in that the bracket additionally includes a slide plate 13 which is guided in grooves 14, which are formed closely underneath the upper side in the wings 3 of the first pair of wings. In the wings 4 of the second pair of wings, short grooves 15 are formed in elongation of the grooves 14 in facing sides of these wings 4, see in particular FIG. 6, into which a partial section of the slide plate 13 may penetrate.

The slide plate 13 has lateral flaps 13a, the length of which being dimensioned such that in the closing position of the slide plate 13, the archwire slot 5 of the bracket is fully covered by the slide plate 13. Moreover, the slide plate 13 has a first hole 16 which is adapted for being engaged by a tool, e.g. a needle for displacing the slide plate 13 between its open and closed positions.

Figure 5:
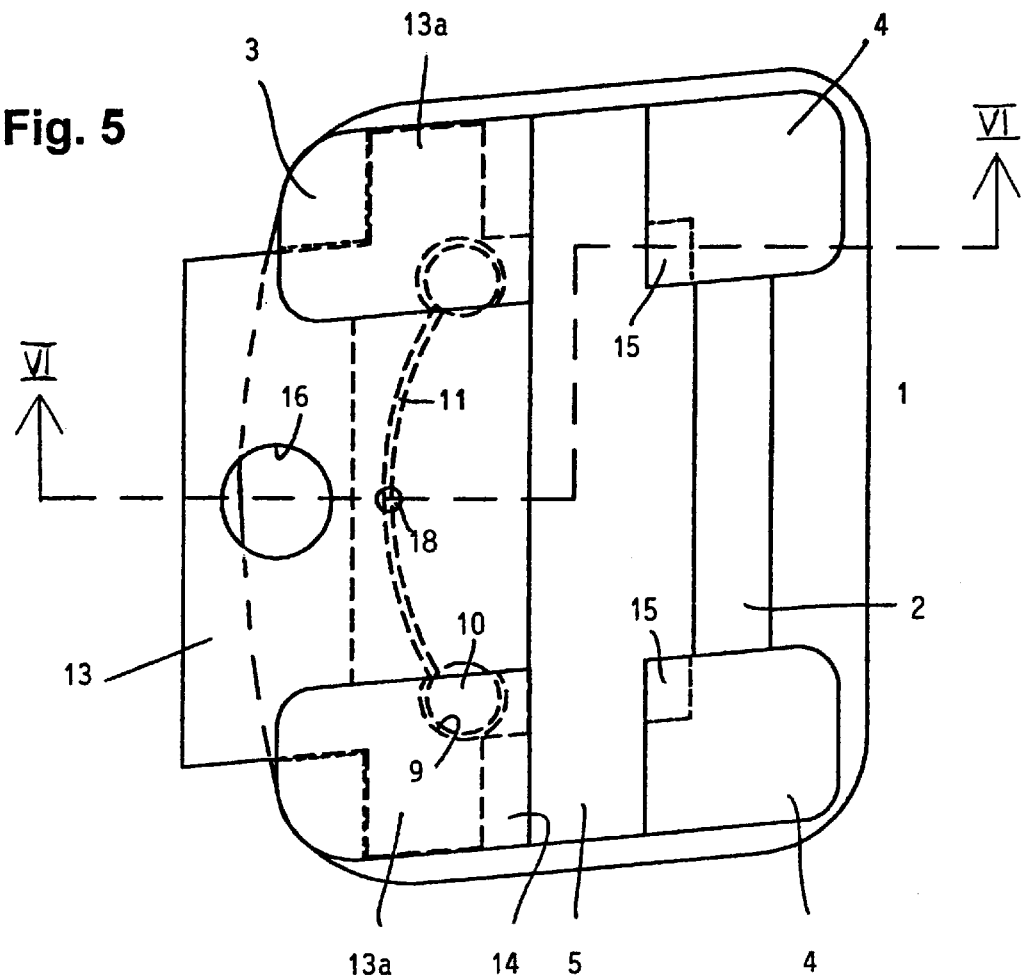
FIG. 5 is a top view onto a bracket according to a second embodiment of the invention in open condition of the pressure spring.
Figure 6:
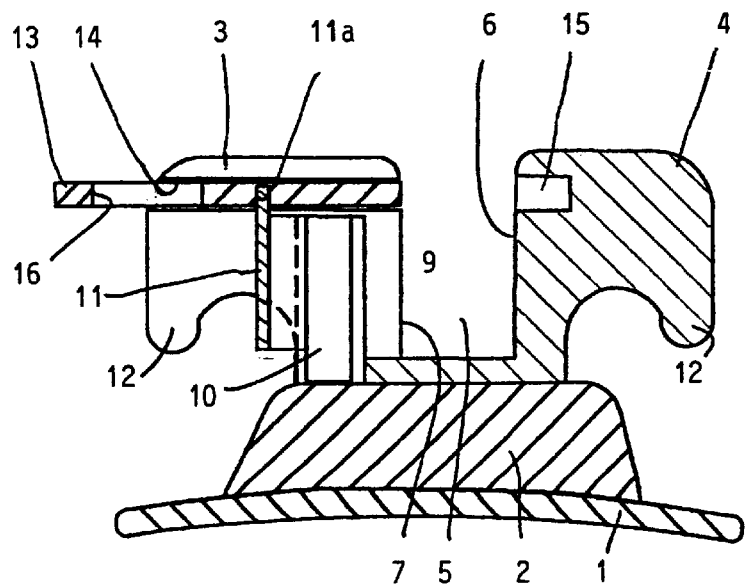
FIG. 6 is a sectional view of the bracket of FIG. 5, cut along the line VI—VI of FIG. 5.

FIG. 5 and 6 show the slide plate 13 and the leaf spring 11 in open condition, in which the archwire slot 15 is fully exposed. In the area located underneath the center of the leaf spring 11, the slide plate 13 has a second, small hole 18, into which a projection 11a formed at the leaf spring 11 engages, which couples the leaf spring 11 with the slide plate 13, see FIG. 6.

Figure 7:
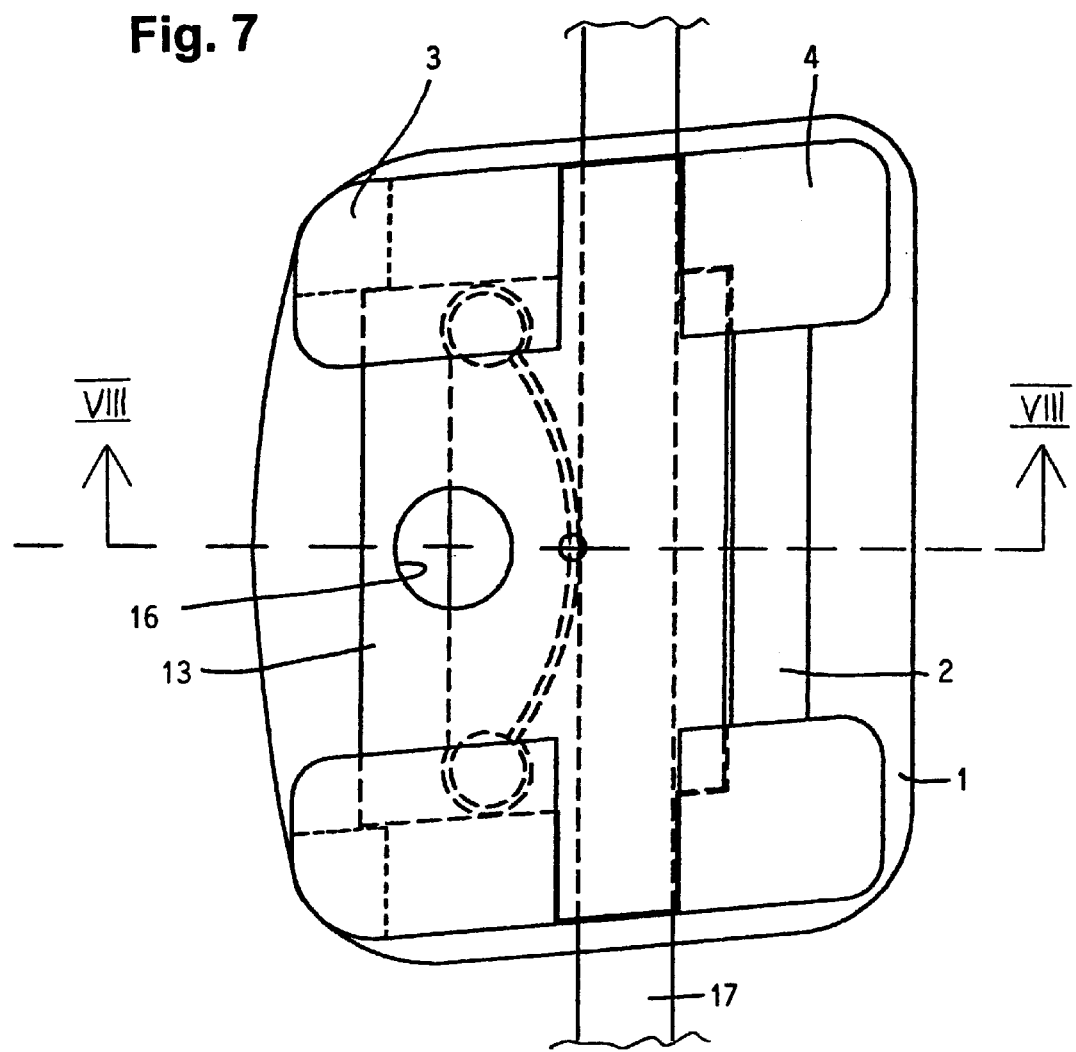
FIG. 7 is a top view onto the bracket of FIG. 5 in closed condition of the pressure spring with an inserted archwire.
Figure 8:
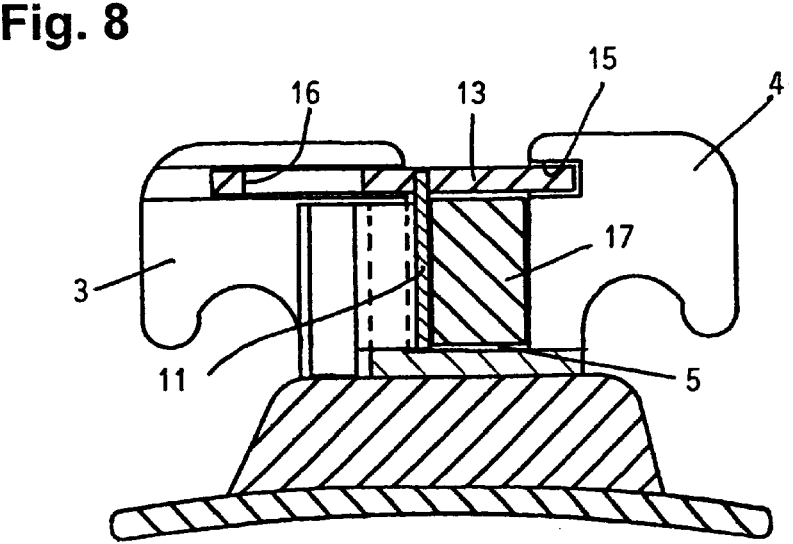
FIG. 8 is a sectional view of the bracket of FIG. 7, cut along the line VIII—VIII of FIG. 7.
Figure 9:
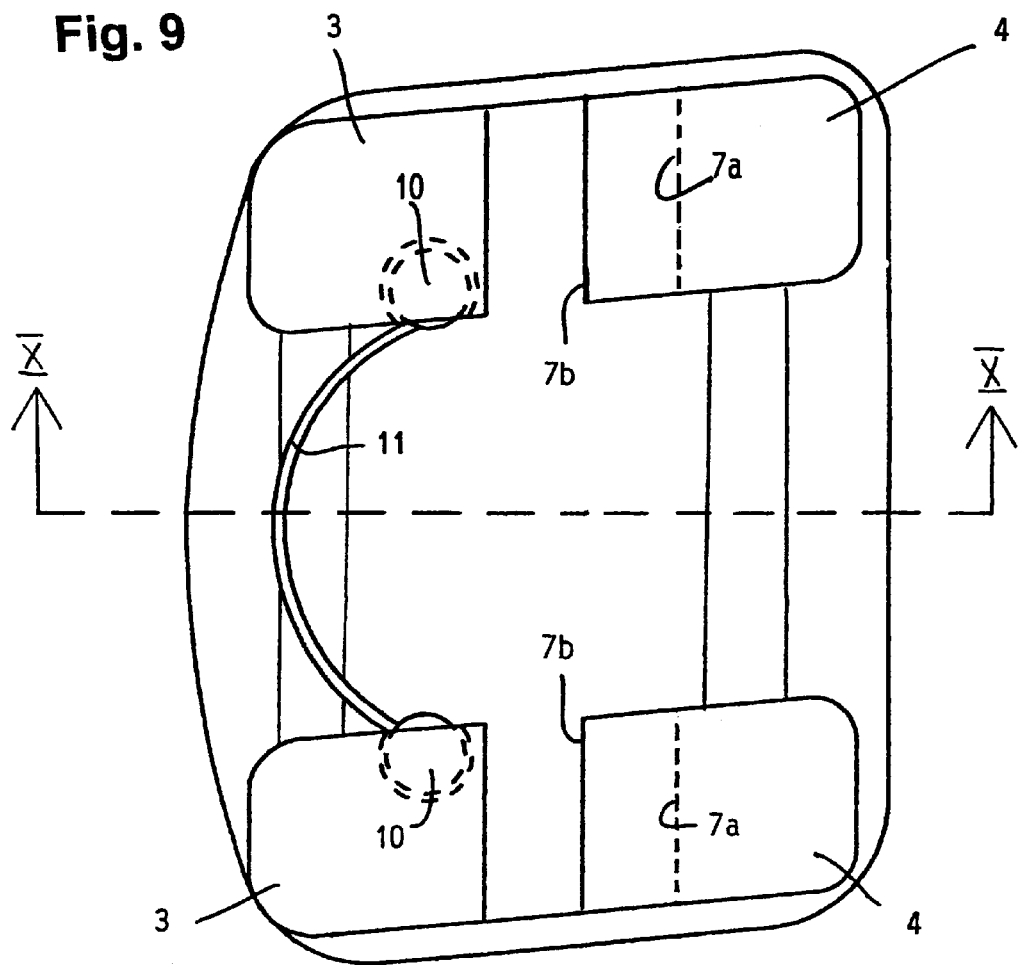
FIG. 9 is a top view onto a bracket according to a third embodiment of the invention in open condition of the pressure spring.
Figure 10:
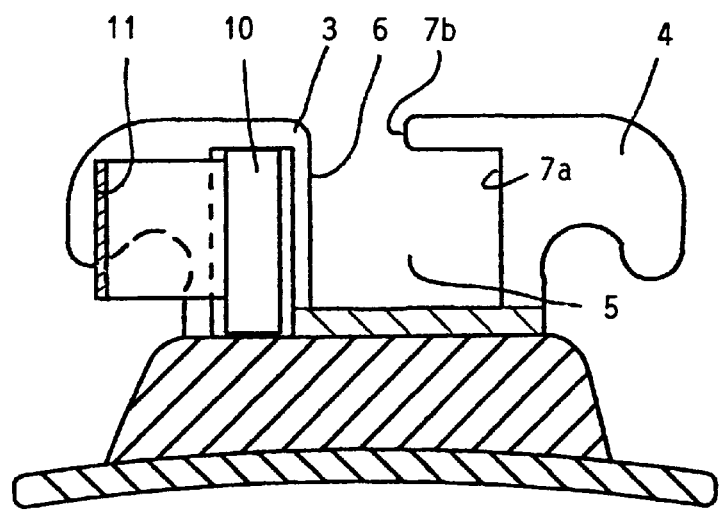
FIG. 10 is a sectional view of the bracket of FIG. 9, cut along the line X—X of FIG. 9.

By means of a tool, e.g. a needle, which is inserted into the hole 16, the slide plate 13 may be brought into the closing position shown in FIG. 7 in which it fully covers the archwire slot 5 and secures an archwire 17 inserted into the slot 5. The front section of the slide plate 13 penetrates into the short grooves 15 at the wings 4 of the second pair of wings. By the coupling of the leaf spring 11 with the slide plate 13, the leaf spring 11 is brought into its second stable position, the closing position, as shown in FIG. 7, in which it also secures the slide plate 13.

The slide plate 13 may consist of metal, it does not have to be resilient and could thus also be made of ceramics. The use of the slide plate 13 renders the use of ligatures superfluous, since the slide plate 13 secures the archwire within the slot 5 against sliding out.

FIG. 9 to 12 show a third embodiment of the invention, which is very similar to the first embodiment. It differs from the first embodiment in that the wings 4 of the second pair of wings have an undercut 7a on the side wall opposite to the leaf spring 11, said undercut being limited toward the top by a projection 7b.

Figure 11:
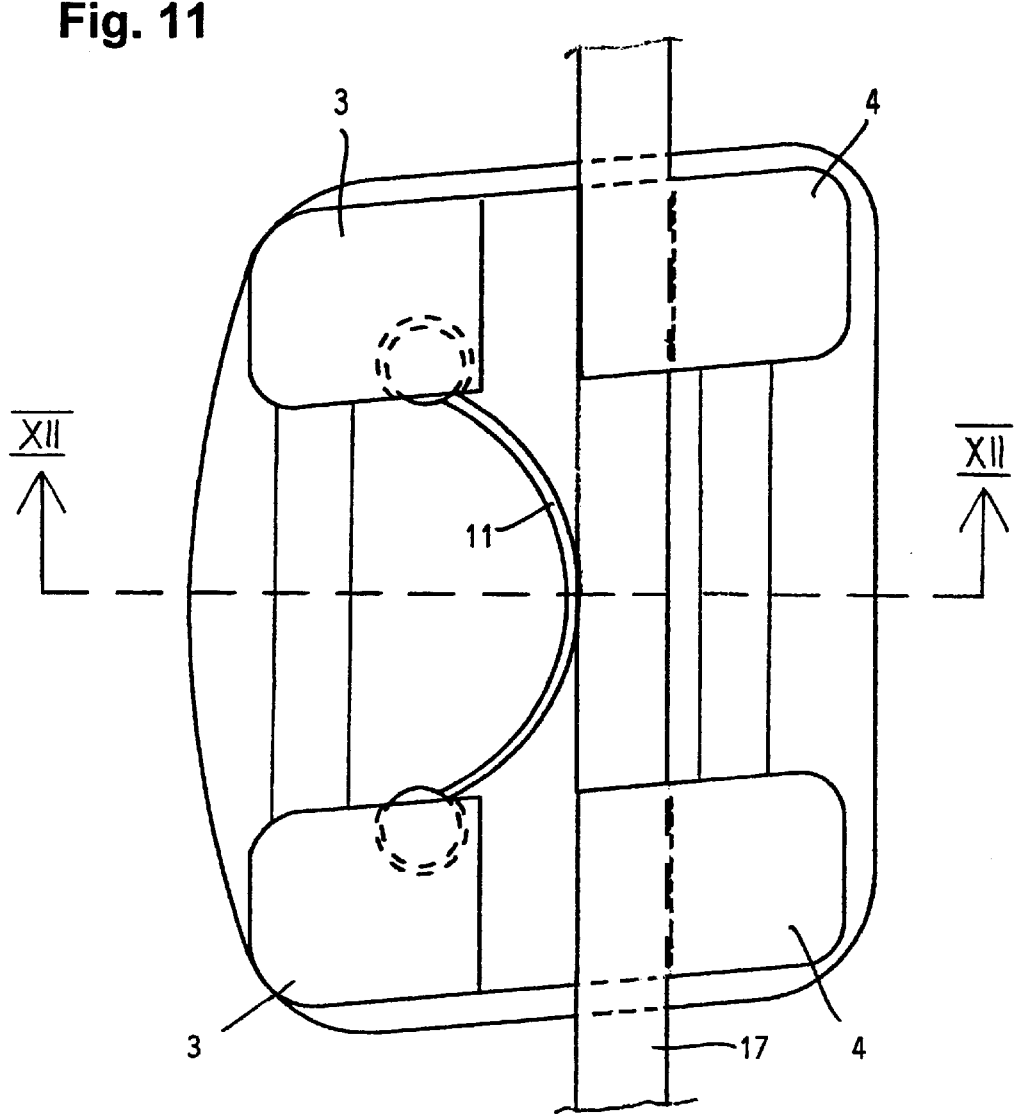
FIG. 11 is a top view onto the bracket of FIG. 9 in closed condition of the pressure spring and with an inserted archwire.
Figure 12:
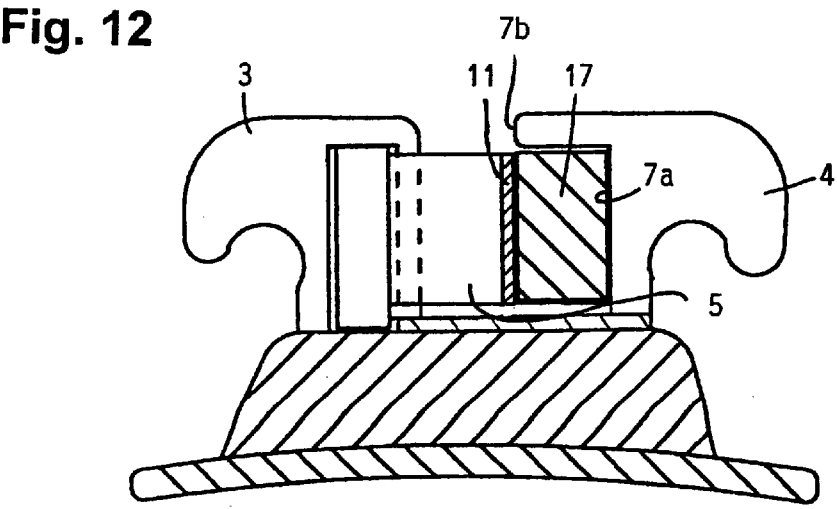
FIG. 12 is a sectional view of the bracket of FIG. 11, cut along the line XII—XII of FIG. 11.
Figure 13:
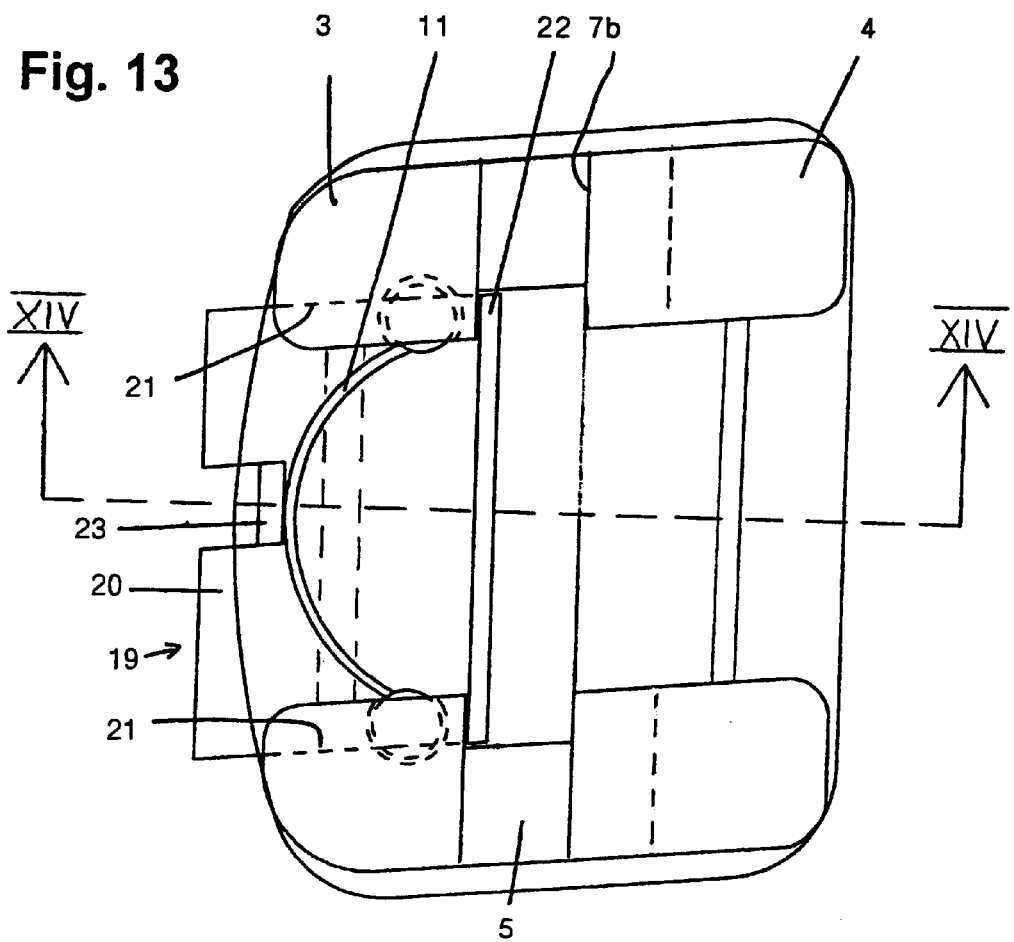
FIG. 13 is a top view onto a fourth embodiment of the invention in open condition of the pressure spring.
Figure 14:
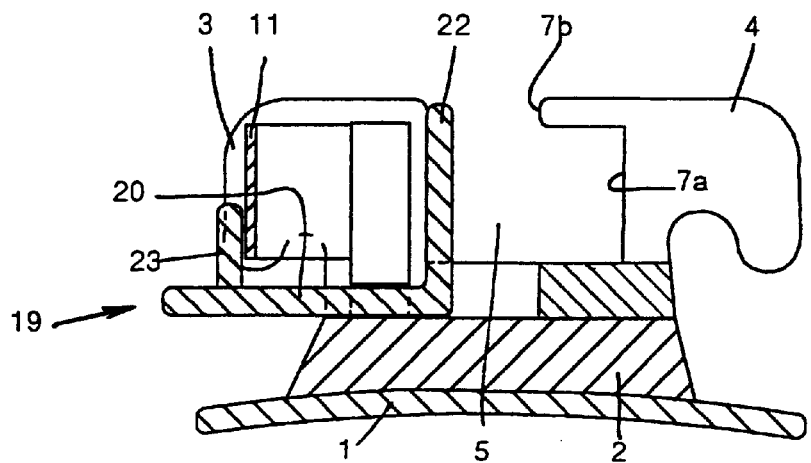
FIG. 14 is a sectional view of the bracket of FIG. 13, cut along the line XIV—XIV of FIG. 13.
Figure 15:
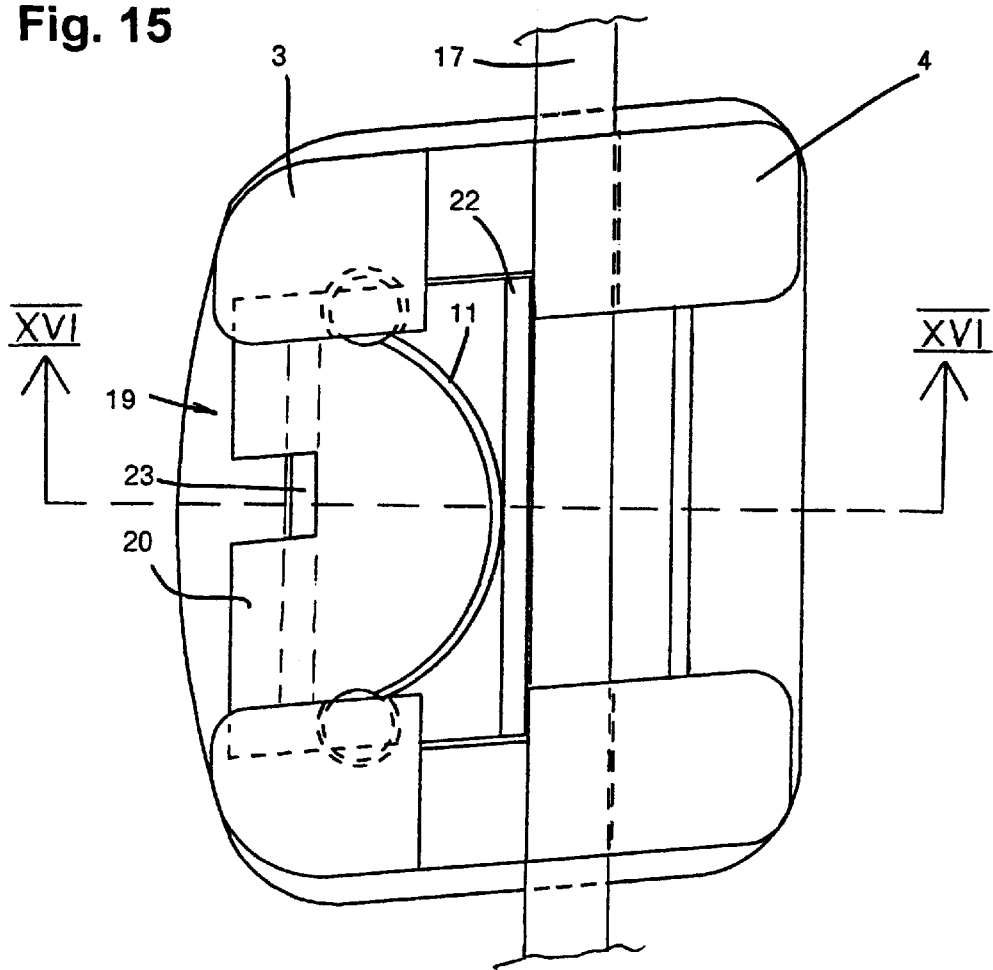
FIG. 15 is a top view onto the bracket of FIG. 13 in closed condition of the pressure spring.
Figure 16:
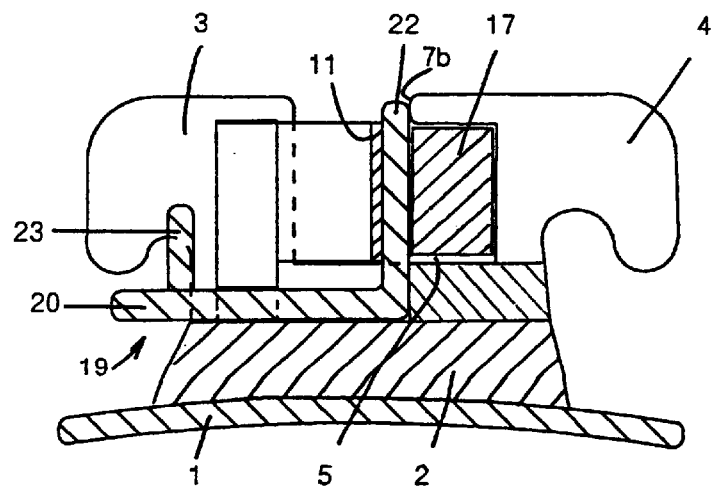
FIG. 16 is a sectional view of the bracket of FIG. 15, cut along the line XVI—XVI of FIG. 15.

As can be learned from FIG. 11 and 12, in which an archwire 17 of a rectangular cross section inserted into the bracket is shown, the archwire is urged underneath the projection 7b into abutment with the undercut in the closing position of the leaf spring 11, so that the archwire is held by the projection 7b in cooperation with the leaf spring 11 in the slot 5 of the bracket. In this embodiment it can therefore be refrained from using ligatures or a slide plate or other means for securing the archwire 17.

FIG. 13 to 16 show a further embodiment of the bracket of FIG. 9 to 12. This bracket differs from that of FIG. 9 to 12 in that the bracket of FIG. 13 to 16 additionally comprises a bent slider 19 extending in parallel to the archwire slot 5 and having a length to span the lateral opening between the wings of both pairs of wings 3 and 4.

Said slider 19 has an L-shaped cross section. One of the flanges, referenced 20, of said slider 19 extends essentially in parallel to the base plate 1 and is slidably guided within grooves 21 formed in the wings 3 of the first pair of wings at the sides facing each other. The other flange, referenced 22, of said slider 19 extends normal to said first mentioned flange 20 and is adapted to be engaged and urged towards the other pair of wings 4 by said leaf spring 11 in the second position thereof.

The flange 20 first mentioned above comprises a tab 23 cut out from the rear edge of said flange and bent upwardly. Said tab 23 is adapted to be engaged by a tool (not shown) for displacing the slider 19 into the closing and open positions and further is adapted to be engaged by the leaf spring 11 in its first (open) position (see FIG. 15) to secure the slider 19 in its open position, comparable to the slider plate 13 in the embodiment of FIGS. 5 to 8.

The slider 19 is made of a rather rigid material. Thus, in view of its length, the slider 19 is able to distribute the force exerted locally only by the leaf spring 11 onto its flange 22 in the second position of the leaf spring onto a considerable length of the archwire 17 disposed in the slot 5, thereby additionally reducing the clearance which may still exist between the archwire and the side wall 7a of the second pair of wings 4. Further, flange 20 of slider 19 due to its length additionally helps securing the archwire in its position under the projections 7b against accidental escape.

FIGS. 17 to 24 show fifth and sixth embodiments of the invention which are modifications of the embodiments shown in FIGS. 1 to 4. Therefore, reference is made to the description thereof to avoid repetitions. The elements in FIGS. 17 to 24 which correspond to those of FIGS. 1 to 4 are designated by the same reference numerals.

Figure 17:
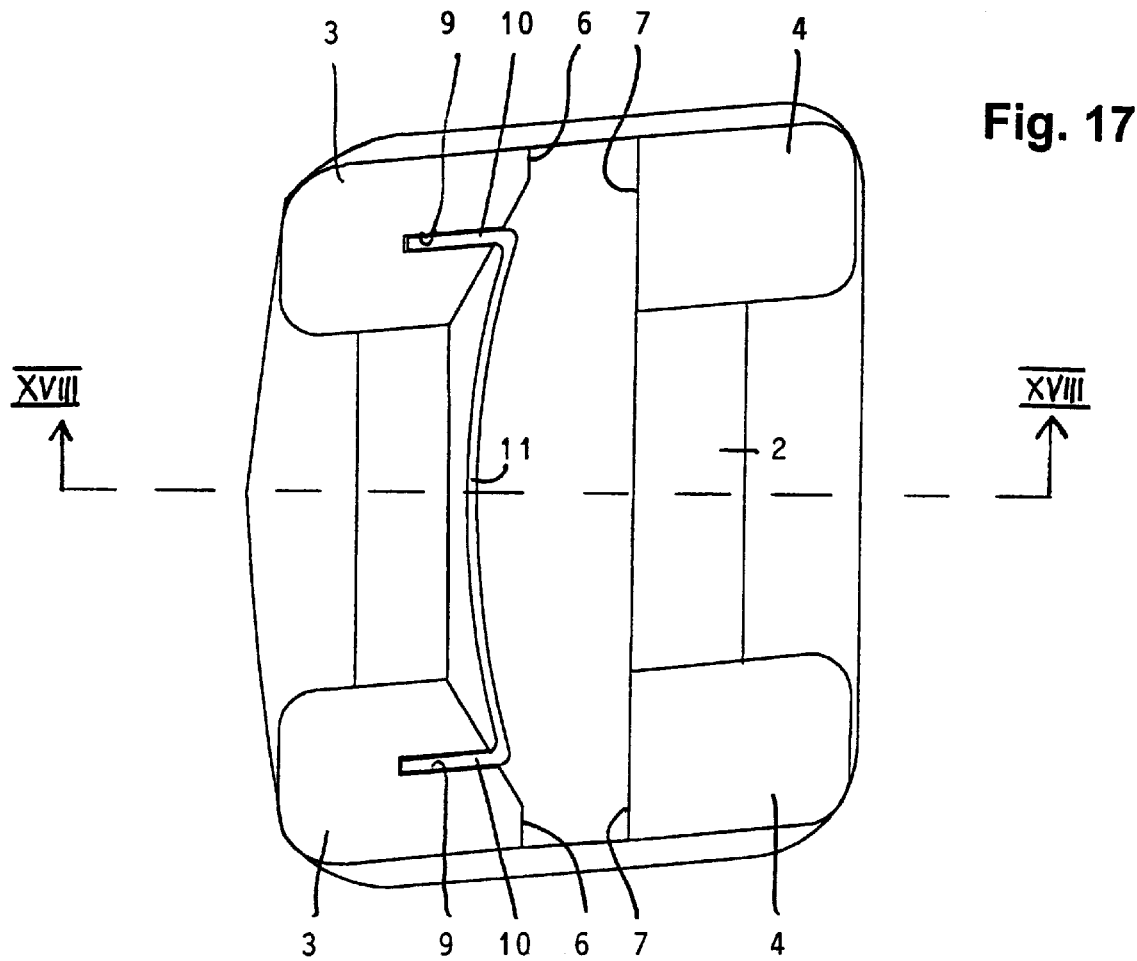
FIG. 17 is a top view of a fifth embodiment of the invention in open condition of the pressure spring.
Figure 18:
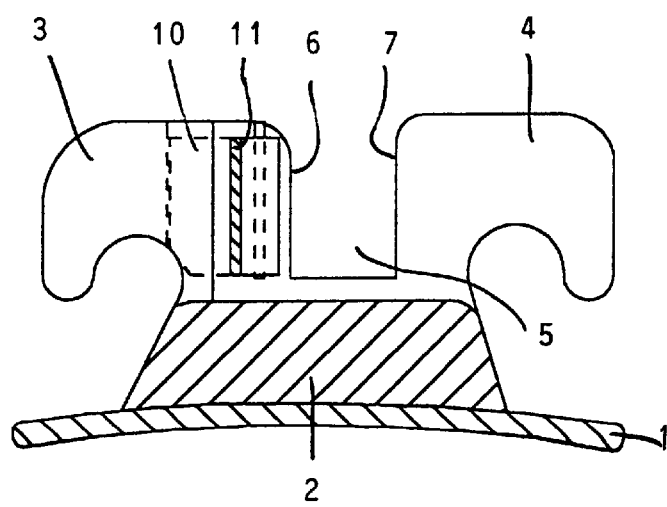
FIG. 18 is a sectional view of the bracket of FIG. 17, cut along the line XVIII—XVIII of FIG. 17.
Figure 19:
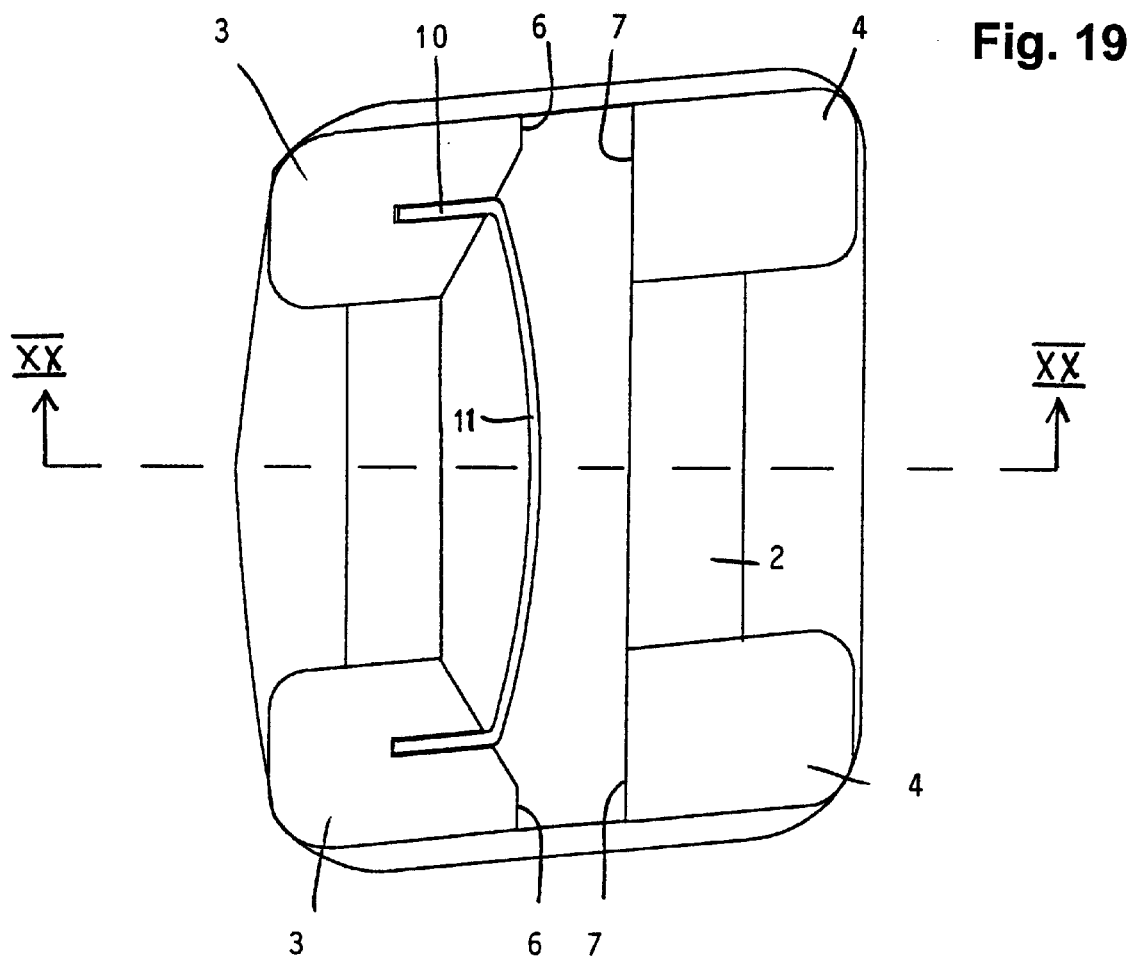
FIG. 19 is a top view of the bracket of FIG. 17 in closed condition of the pressure spring.
Figure 20:
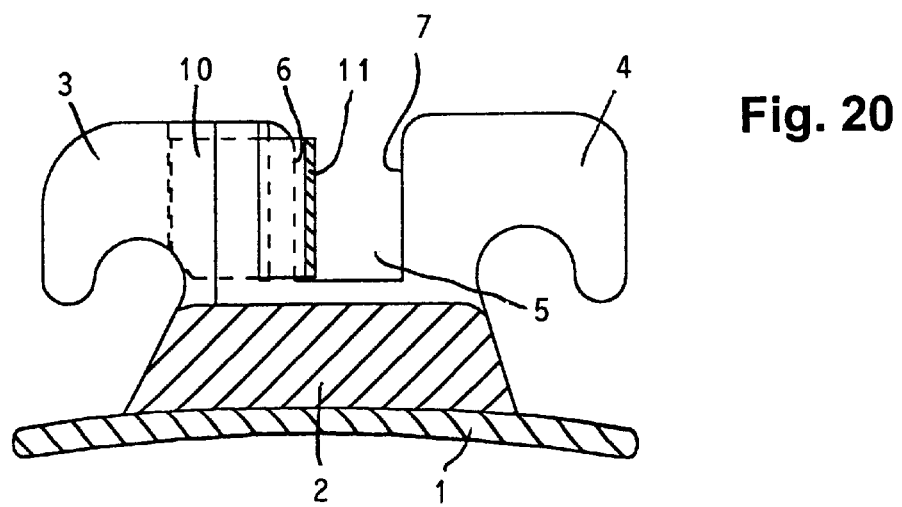
FIG. 20 is a sectional view of the bracket of FIG. 19, cut along the line XX—XX of FIG. 19.

The fifth embodiment of FIG. 17 to 20 differs from the first embodiment in that the ends 10 of the leaf spring 11 are not rolled but are bent in a direction extending substantially transversally to the longitudinal extension of the leaf spring 11. The bearings 9 in which those ends 10 are seated are formed as narrow gaps formed in a side wall 6 of the slot 5 and extending substantially orthogonally to the longitudinal extension of said slot 5. It is to be noted that the distance between those gaps is smaller than the distance of said bent ends 10 of the leaf spring 11 from one another in unmounted condition of the leaf spring, so that upon installation of the leaf spring at the bracket structure the leaf spring will adopt an arc shape and will have two stable conditions of which a first one shown in FIG. 17 is the open condition and a second one shown in FIG. 18 is the closed condition.

The material of the wings 3 and 4 delimiting said gaps may be calked after mounting of the leaf spring 11 so as to permanently fix the leaf spring 11 at the bracket structure.

The sixth embodiment of FIGS. 21 to 24 differs from the first embodiment of FIGS. 1 to 4 in that the ends 10 of the leaf spring 11 are bent in a direction extending substantially transversally to the longitudinal extension of the leaf spring 11, as in the fifth embodiment.

Figure 21:
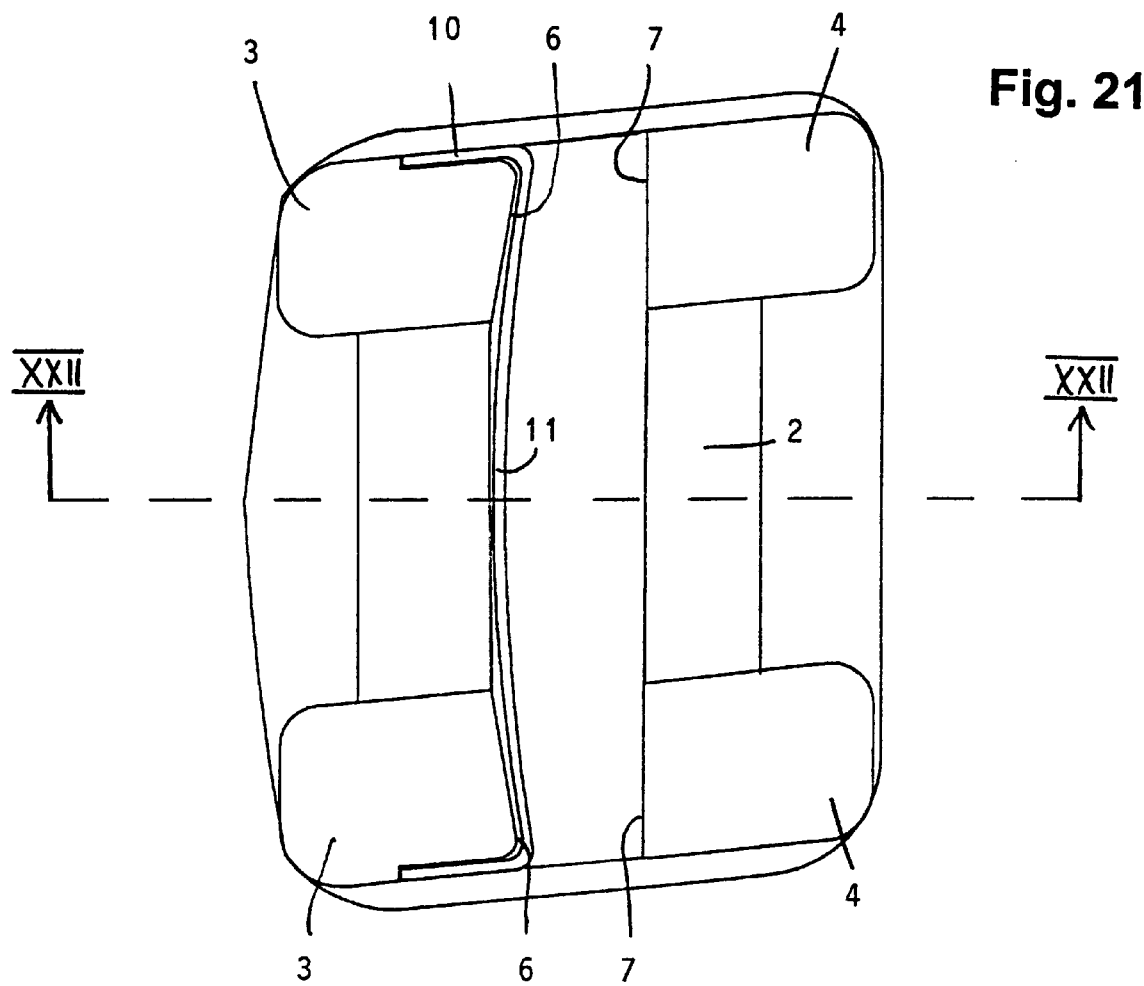
FIG. 21 is a top view of a sixth embodiment of the invention in open condition of the pressure spring.
Figure 22:
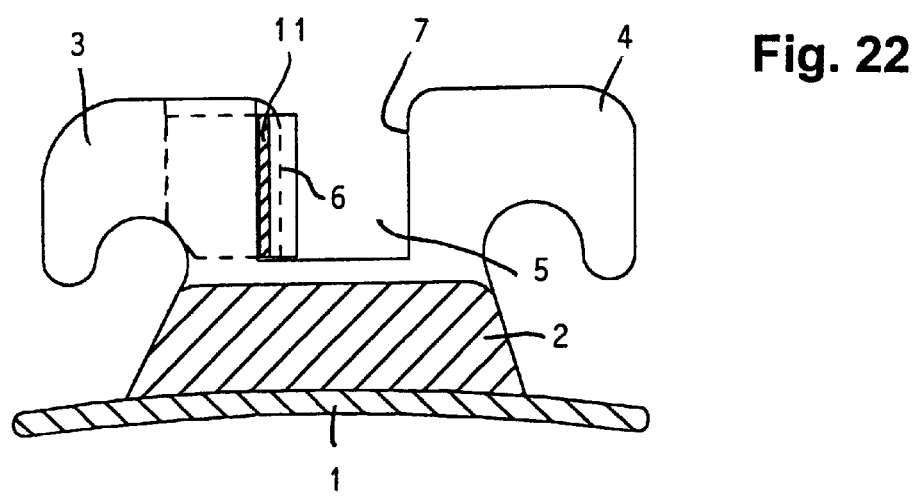
FIG. 22 is a sectional view of the bracket of FIG. 20, cut along the line XXII—XXII of FIG. 21.
Figure 23:
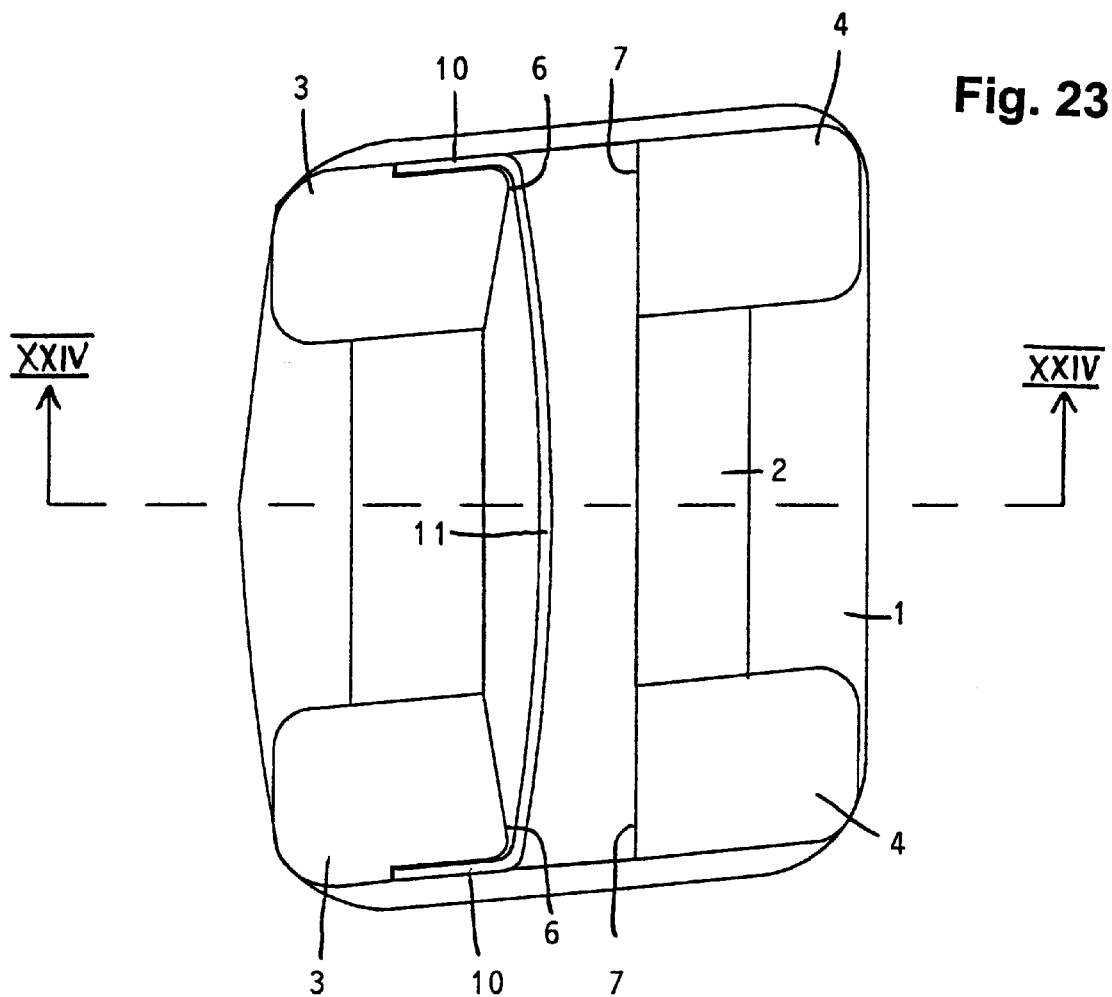
FIG. 23 is a top view of the bracket of FIG. 21 in closed condition of the pressure spring.
Figure 24:
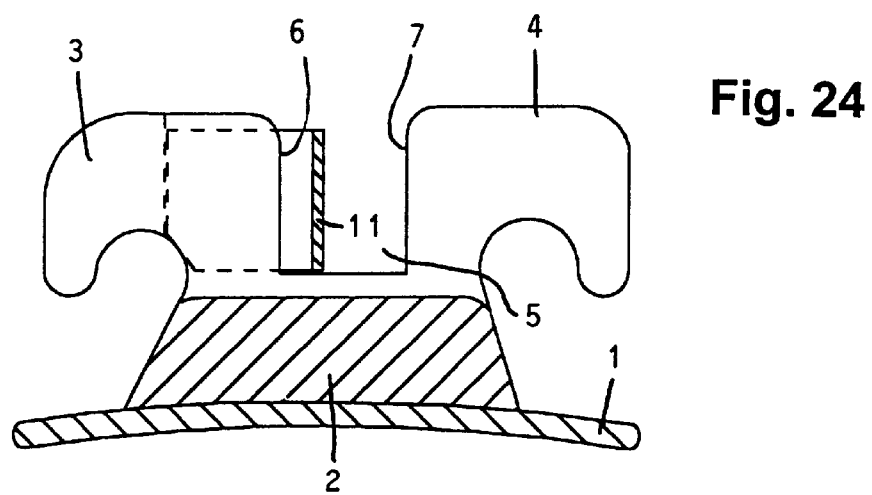
FIG. 24 is a sectional view of the bracket of FIG. 23, cut along the line of XXIV—XXIV of FIG. 23.

Those bent ends 10 of the leaf spring are attached, preferably by welding, to end faces of the wings 3 and 4 where the slot 5 ends, i.e. at regions outside said slot 5, so that the longitudinal extension of the leaf spring 11 extends over the whole length of the slot 5. It goes without saying that the distance between the bent ends 10 of the leaf spring 11 in disassembled condition thereof is larger than the length of the slot so that upon mounting the leaf spring 11 at the bracket structure it adopts an arc shape having two stable conditions of which the open condition is shown in FIG. 21 and the closed condition is shown in FIG. 23.

In FIGS. 17 to 24, the arch wire is not shown as it is not necessary for the explanation of those embodiments of the invention.

In the embodiments of FIGS. 17 to 24, the side wall of the slot where the leaf spring is fixed is formed with an arcuate or wedge shaped recess to allow the unimpeded forming of an arc by the leaf spring in the open condition thereof.

The benefit of the fifth and sixth embodiment over the first embodiment is that at a given length of the slot, i.e. length of the bracket structure, the leaf spring 11 is longer than that of the embodiment of FIGS. 1 to 4, so that the manufacture of the bracket may become easier.

It is to be noted that a bracket having the leaf spring design and mounting of the fifth and sixth embodiments may also be formed with a slide plate comparable to the embodiments of FIGS. 5 to 8 to close the slot.

It is further to be noted that a bracket having the leaf spring design and mounting of the fifth and sixth embodiments may also be formed with an undercut at the wings on the side wall opposite to the leaf spring, as is shown in the embodiment of FIGS. 9 to 12 to secure the arch wire at the bracket without any need for ligatures.

Finally, it is to be noted that a bracket having the leaf spring design and mounting of the fifth and sixth embodiments may also be provided with a bent slider as shown in the embodiment of FIGS. 13 to 16 to span the lateral opening between the wings of both pairs of wings.

For the explanation of these modifications of the fifth and sixth embodiments, reference is made to the explanation given to FIGS. 9 to 16 to avoid repetitions.

I claim:

1. An orthodontic bracket, comprising a base plate for attachment to a crown of a tooth and a structure secured to an upper side of the base plate and raising over the base plate, said structure comprising at least one slot open toward a top of said bracket and limited by a bottom wall and side walls and which is adapted to receive an archwire, wherein a pressure spring is supported at the bracket which is adapted for causing a force at an archwire inserted into the slot, said force acting in a direction towards one of the side walls limiting the slot, said pressure spring being an arc-shaped leaf spring, the ends of which are supported at said structure at positions spaced along the slot.

2. An orthodontic bracket as set forth in claim 1, wherein the ends of said arc-shaped leaf spring are supported in recesses formed in said structure.

3. An orthodontic bracket as set forth in claim 2, wherein said recesses are slots formed in the other one of said side walls and extend transversally to said slot, the ends of said arc-shaped leaf spring being bent in a direction extending substantially transversely to a longitudinal extension of said leaf spring.

4. An orthodontic bracket as set forth in claim 3, wherein the ends of said arc-shaped leaf spring are fixed in said recesses by calking a material of said structure delimiting said recesses at said structure.

5. An orthodontic bracket as set forth in claim 1, wherein the ends of said arc-shaped leaf spring are fixedly attached to said structure at end positions thereof where said slot ends.

6. An othodontic bracket as set forth in claim 5, wherein the ends of said arc-shaped leaf spring are welded to said end portions of said structure.

7. An orthodontic bracket as set forth in claim 1, wherein the structure of the bracket has an opening at both sides of the slot, so that the structure forms two pairs of wings which laterally limit the slot, and the leaf spring is clamped between the wings of one of the pair of wings.

8. An orthodontic bracket as set forth in claim 7, wherein a slide plate is displaceably supported at the bracket, said slide plate being movable into a position covering the slot and being mechanically coupleable to the leaf spring.

9. An orthodontic bracket as set forth in claim 1, wherein a slide plate is displaceably supported at the bracket, said slide plate being movable into a position covering the slot and being mechanically coupleable to the leaf spring.

10. An orthodontic bracket as set forth in claim 1, wherein the side of the structure opposite the pressure spring comprises an undercut which is limited in a direction opposite the base plate by a projection which is adapted to hold an archwire inserted into the slot.

11. An orthodontic bracket as set forth in claim 10, further comprising a bent slider having a first flange slidably guided in grooves provided at the structure at positions facing each other, and having a second flange normal to said first flange, said second flange being adapted to be engaged by the pressure spring so as to be laterally urged against an archwire inserted into the slot and held therein by said projection.

12. An othodontic bracket as set forth in claim 11, wherein the first flange of the bent slider comprises a cut out at the edge opposite the second flange, said cut out forming a tab which is bent upwardly and engageable by said leaf spring in a position disengaged from an archwire inserted into the slot.

* * * * *